(12) United States Patent
Nedez

(10) Patent No.: US 6,174,480 B1
(45) Date of Patent: Jan. 16, 2001

(54) METHOD FOR ELIMINATING INHIBITORS OF POLYMERIZATION OF MONOMER MIXTURES USING AN ALUMINA WITH OPTIMIZED FORM

(75) Inventor: Christophe Nedez, Salindres (FR)

(73) Assignee: Rhodia Chimie, Courbevoie Cedex (FR)

( * ) Notice: Under 35 U.S.C. 154(b), the term of this patent shall be extended for 0 days.

(21) Appl. No.: 09/341,956

(22) PCT Filed: Jan. 13, 1998

(86) PCT No.: PCT/FR98/00053
§ 371 Date: Sep. 9, 1999
§ 102(e) Date: Sep. 9, 1999

(87) PCT Pub. No.: WO98/32717
PCT Pub. Date: Jul. 30, 1998

(30) Foreign Application Priority Data

Jan. 22, 1997 (FR) .................................................. 97 00625

(51) Int. Cl.[7] ........................................................ B28B 3/20

(52) U.S. Cl. ........................ 264/176.1; 528/271; 528/272; 528/485

(58) Field of Search ..................................... 528/271, 272, 528/48 S; 264/176.1

(56) References Cited

U.S. PATENT DOCUMENTS 3,240,830  3/1966  Dye ...................................... 528/176

FOREIGN PATENT DOCUMENTS 1 361 512  4/1964  (FR) .
2 248 627  4/1992  (GB) .

Primary Examiner—Terressa M. Boykin
(74) Attorney, Agent, or Firm—Burns, Doane, Swecker & Mathis, L.L.P.

(57) ABSTRACT

The invention relates to a process for adsorption of polymerization inhibitors from ethylenically unsaturated monomers, in which these inhibitors are placed in contact with an alumina produced by forming by drop coagulation or by extrusion-blending.

17 Claims, No Drawings

METHOD FOR ELIMINATING INHIBITORS OF POLYMERIZATION OF MONOMER MIXTURES USING AN ALUMINA WITH OPTIMIZED FORM

The present invention relates to a new process for removing polymerization inhibitors from monomer mixtures, especially from ethylenically unsaturated monomers.

In the industry of polymerization of a large number of ethylenic monomers an important problem has to do with the storage and/or transport of these monomers. This is because an uncontrolled spontaneous polymerization of these monomers in the course of time, starting from free radicals, can be observed. These ethylenically unstable monomers are especially those which have a second unsaturation such as a COOH, C=O, C≡N, C=C, C=S or C=N functional group; they may be, for example, the following monomers: styrene, butadiene, isoprene, (meth)acrylic esters, acrylonitrile, acrolein, chloroprene, vinyl acetate, etc.

To avoid this degradation of the monomers it is known to stabilize them by means of inhibiting substances which prevent polymerization from taking place.

These substances, more generally known as "polymerization inhibitors" can be chosen from picric acid, nitroaromatics, quinone derivatives (hydroquinone, benzoquinone), naphthols, amines (p-phenylenediamine, phenothiazine), phosphites, p-methoxyphenol, p-tert-butylcatechol, etc.

When is it desired to employ inhibited monomers in order to polymerize them or to use them in chemical reactions, it is often necessary to remove the polymerization inhibitors. A number of means are employed for this purpose:

- it is possible to add a large quantity of initiator to the reactor to combat the effect of the inhibitor; however, this technique is not suitable in every case,
- the temperature can be raised considerably to produce the thermolysis of the inhibitor, but the monomer must have a high thermal stability,
- the charge of monomers and of inhibitor can be distilled, but the monomer must exhibit good thermal stability; in addition, such an operation is difficult to carry out on an industrial scale, and the boiling point of the inhibitor is in many cases higher than that of the monomer,
- the inhibitor can be removed by adding a dilute solution, for example of sodium hydroxide, the monomer charge being subsequently washed with water in order to remove all traces of caustic compounds; however, the treatment of the liquid effluents also presents industrial problems,
- lastly, the inhibitor can be adsorbed with the aid of a compound such as alumina, silica gel, activated carbon, calcium oxide, aluminium silicate, talc, calcium sulphates, magnesium sulphates, copper sulphates, magnesium silicate clays, a resin etc.

Adsorption is one of the most advantageous methods because it does not exhibit any of the abovementioned disadvantages. Among the adsorbents employed, activated alumina is preferred.

The objective of the present invention is to propose a new alumina for the adsorption of polymerization inhibitors from ethylenically unsaturated monomers, exhibiting adsorption capacities which are improved in relation to the aluminas of the prior art.

To this end the invention relates to a process for adsorption of polymerization inhibitors from ethylenically unsaturated monomers, in which these inhibitors are placed in contact with an alumina, the said alumina being produced by forming by drop coagulation or by extrusion-blending.

The principle of the invention therefore relates to the manner in which the alumina has been prepared, very particularly concerning its forming. The purification process according to the invention thus uses an alumina which can be obtained in accordance with a number of forming methods.

According to a first method the alumina employed may be in the form of alumina beads. These beads are produced by forming using drop (or oil-drop) coagulation. This forming consists in introducing drops of an aqueous solution based on an aluminium compound into a water-immiscible liquid (oil, kerosene, etc.) in such a way that the drops form substantially spherical particles and these particles are coagulated simultaneously with and/or after the spheroidal forming, by a gelling agent. The beads are subsequently recovered and then dried and calcined.

Beads of this type can be prepared, for example, according to the process described in patent EP-A-097 539, or by coagulation as drops of a suspension or of an aqueous dispersion of alumina or of a solution of a basic aluminium salt which is in the form of an emulsion consisting of an organic phase, an aqueous phase and a surface agent or an emulsifier. The said organic phase may in particular be a hydrocarbon; the surface-active or emulsifying agent is, for example, Galoryl EM 10®.

These beads can also be prepared according to the process described in patent EP-A-015 801 by mixing, at a pH lower than 7.5, an ultrafine boehmite sol and spheroidal alumina particles, then drop coagulation of this mixture as indicated above and, finally, drying and calcining.

According to this first method using beads, the latter must not originate from a process of forming alumina using a rotational technique. A rotational technique is intended to mean any equipment in which the agglomeration is performed by bringing into contact and rotating the product to be granulated about itself. Equipment of this type which may be mentioned is the rotary coating pan and the rotating drum.

It has been noted that these alumina beads exhibit inferior properties for the adsorption of corrosion inhibitors, compared with the alumina beads employed in the present invention.

According to a second method of the invention, alumina extrudates may also be involved. These are generally obtained by blending and then extruding an alumina-based material and, lastly, calcining. The starting material may be of very varied nature: it may be produced by partial and rapid dehydration of hydrargillite, according to the teaching of application FR-A-1,108,011, or by the precipitation of boehmite, pseudoboehmite, bayerite alumina or of a mixture of these aluminas. During the blending the alumina may be mixed with additives such as pore-formers. To give an example, the extrudates may be prepared by the process of preparation described in U.S. Pat. No. 3,856,708.

In general, it is preferred to employ alumina extrudates rather than beads produced by drop coagulation.

These extrudates may exhibit all kinds of shapes: solid or hollow cylinders, multilobes, etc.

The alumina employed in the process according to the invention preferably has a total pore volume (TPV) of at least 0.2 ml/g, preferably of at least 0.3 ml/g.

This total pore volume (TPV) is measured as follows. The value of the grain density and of the absolute density is determined, the grain (Dg) and absolute (Da) densities being measured by the pycnometry method with mercury and with helium respectively. The TPV is then given by the formula:

$$\frac{1}{Dg} - \frac{1}{Da}$$

In general, aluminas of particle size of between 0.8 and 10 mm, preferably between 1 and 5 mm, are used. In the case of forming by drop coagulation the particle size corresponds to the bead diameter and, in the case of extrudates, to the diameter of their cross-section.

The alumina preferably has a specific surface of at least 10 $m^2/g$, or even of at least 50 $m^2/g$.

This specific surface is a surface measured by the BET method.

A surface measured by the BET method is intended to mean the specific surface determined by nitrogen adsorption in accordance with ASTM Standard D 3663-78, established from the Brunauer—Emmett—Teller method described in the periodical "The Journal of the American Chemical Society", 60, 309 (1938).

The process according to the invention preferably uses an alumina including at least one compound of an element chosen from the alkali metals, the rare earths and the alkaline-earth metals.

This compound may be an oxide, a hydroxide, a salt or a mixture of these. For example, in addition to hydroxides, the sulphates, nitrates, halides, acetates, formates, carbonates and carboxylic acid salts may be mentioned.

Elements chosen from sodium, potassium, lithium, lanthanum and cerium are preferably employed.

The content of alkali metal, alkaline-earth metal or rare-earth element is generally at least 5 mmol per 100 g of alumina, preferably at most 400 mmol, more preferably still between 10 and 400 mmol.

According to a preferred alternative form the alkali metal element is sodium and its content is between 15 and 300 mmol per 100 of alumina.

The deposition of the compound of the dopant element on or in the alumina can be carried out by any method known to a person skilled in the art. It may be carried out, for example, by impregnation of the alumina already prepared with the alkali metal, rare-earth or alkaline-earth metal elements or precursors of these elements, or by mixing the alkali metal, rare-earth or alkaline-earth metal elements or precursors with alumina in the course of the forming of these materials. These elements may also be introduced into the alumina by coprecipitation of the alumina and of the alkali metal, rare-earth or alkaline-earth metal elements or of their precursors.

The alumina used in the process of the invention is preferably prepared by:

impregnation of alumina with a solution of a compound of an element or of a mixture of compounds, drying of the said impregnated alumina, heat treatment of the said alumina.

The impregnation is carried out in a known manner by placing the alumina in contact with a solution, a sol or a gel including at least one alkali metal, rare-earth or alkaline-earth metal element in the form of oxide or salt or of one of their precursors.

The operation is carried out in general by soaking the alumina in a determined volume of solution of at least one precursor of an alkali metal, rare-earth or alkaline-earth metal element. Solution of a precursor of one of these elements is intended to mean a solution of a salt or a compound of the element or of at least one of the alkali metal, rare-earth or alkaline-earth metal elements, it being possible for these salts and compounds to be thermally decomposed to oxides.

The salt concentration of the solution is chosen as a function of the quantity of element to be deposited on the alumina.

According to a preferred method these elements are deposited by dry impregnation, that is to say that the impregnation is carried out with just the volume of solution needed for the said impregnation, without excess.

The heat treatment is carried out at a temperature determined as a function either of the temperature of use of the alumina or of the desired specific surface. It may also be possible to carry out a heat treatment to obtain an at least partial thermal degradation of the compound, for example in oxide form. However, this degradation is not necessary and, to give an example, it is not necessary especially when compounds such as chlorides, nitrates or hydroxides are employed.

The heat treatment may, for example, be carried out at a temperature which is between 150 and 1000° C., preferably between 300 and 800° C.

The adsorption process according to the invention is suitable when the polymerization inhibitor is chosen, for example, from picric acid, nitroaromatics, quinone derivatives (hydroquinone, benzoquinone), naphthols, amines (p-phenylenediamine, phenothiazine), phosphites, p-methoxyphenol and p-tert-butylcatechol. Particularly good results are obtained for the adsorption of p-tert-butylcatechol.

When purifying an ethylenically unsaturated monomer stabilized with a polymerization inhibitor is involved, the alumina is placed in contact with the said mixture of ethylenically unsaturated monomer and inhibitor, for example at ambient temperatures.

The monomer charge may be based on any type of ethylenically unsaturated monomer such as especially: styrene, butadiene, isoprene, vinyl chloride, vinylidene chloride, tetrafluoroethylene, trifluorochloroethylene, chloroprene, allyl alcohol, vinyl ether, vinyl ester (vinyl acetate), alkyl acrylates and methacrylates (methacrylate, butyl acrylate, ethyl acrylate, 2-ethylhexyl acrylate, methyl methacrylate, ethyl methacrylate, 2-ethylhexyl methacrylate, etc.), acrolein, acrylonitrile, acrylamide, vinylamine, etc., or mixtures thereof.

In general, the mixture of ethylenically unsaturated monomer and of inhibitor includes 2 to 2000 ppm by weight per volume of inhibitor, preferably 5 to 1500 ppm.

The following examples illustrate the invention without, however, limiting its scope.

EXAMPLES

Example 1

The alumina samples tested are pretreated under a stream of air of nitrogen at 300° C. for 2 hours in order to remove any trace of moisture following their storage and in order to make it possible to compare their effectiveness in identical conditions.

1 g of alumina (solids content) thus pretreated is introduced into 200 ml of a solution of cyclohexane containing 500 or 1000 ppm (by weight/volume) of p-tert-butylcatechol (TBC). The temperature is maintained at 25° C. The content of TBC present in the solution is analysed, in the course of time, by UV-visible.

The degree of adsorption of TBC is deduced from this.

The characteristics of the aluminas employed are combined in Table 1.

TABLE 1

| Alumina* | Forming* | Particle size (mm) | BET surface ($m^2/g$) | TPV (ml/g) |
|---|---|---|---|---|
| 1 | RT | 1.4–2.8 | 328 | 0.50 |
| 2 | DC | 1.8–2.1 | 190 | 0.61 |
| 3 | EB | 1.6 | 231 | 0.60 |
| 4 | EB | 1.6 | 402 | 0.385 |
| 5 | EB | 1.2 | 215 | 0.545 |
| 6 | EB | 1.2 | 207 | 0.60 |

Forming*:
RT: rotational technique
EB: extrusion/blending
DC: drop coagulation
Aluminas*:
Alumina 1: Activated alumina 1.5/3 marketed by Procatalyse
Alumina 2: Spheralite 537 marketed by Procatalyse
Alumina 3: Spheralite 521E marketed by Procatalyse
Alumina 5: Spheralite 521 marketed by Procatalyse The results obtained according to the TBC contents (500 or 1000 ppm) for the various aluminas appear in Tables 1 and 2.

TABLE 1

1000 ppm of TBC

% of TBC adsorbed

| Time | Alumina 1 | Alumina 3 | Alumina 4 | Alumina 5 | Alumina 6 |
|---|---|---|---|---|---|
| 0 | 0 | 0 | 0 | 0 | 0 |
| 21 h 50 | 12.7 | | | 61.8 | |
| 65 h | 30.5 | | | 76.6 | |
| 69 h | | 73.9 | 45.6 | | 62.7 |
| 162 h | 44.3 | 79.9 | 61.1 | 78.2 | 63.5 |

TABLE 2

500 ppm of TBC

% of TBC adsorbed

| Time (hours) | Alumina 1 | Alumina 2 | Alumina 5 |
|---|---|---|---|
| 0 | 0 | 0 | 0 |
| 2 | 15.5 | | |
| 5 | 20.5 | | |
| 16.50 | 29.1 | | |
| 21 | | 80.5 | 73.7 |
| 21.25 | 31.2 | | |
| 29 | 35.1 | | |
| 40.75 | 36.3 | | |
| 47.50 | 37.0 | | |
| 64 | 40.7 | | |
| 71 | | 95.2 | 92.4 |
| 88.50 | 46.0 | | |
| 136 | 52.2 | | |
| 162 | | 99.2 | 97.6 |

Example 2

The alumina samples tested are pretreated under a stream of air of nitrogen at 300° C. for 2 hours in order to remove any trace of moisture following their storage and in order to make it possible to compare their effectiveness in identical conditions.

1 g of alumina (solids content) thus pretreated is introduced into 200 ml of a solution of styrene containing 500 ppm (by weight/volume) of p-tert-butylcatechol (TBC). The temperature is maintained at 25° C. After 21 hours the proportion of TBC present in the solution is analysed by UB-visible.

The degree of adsorption of TBC is deduced from this.

The characteristics of the aluminas employed are combined in Table 2.

TABLE 2

| Alumina* | Forming* | Particle size (mm) | BET surface ($m^2/g$) | TPV (ml/g) | % TBC adsorbed after 21 h |
|---|---|---|---|---|---|
| 1 | RT | 1.4–2.8 | 328 | 0.50 | 31 |
| 5 | EB | 1.2 | 215 | 0.545 | 81 |

Example 3

A commercial alumina is treated with a potassium compound. The starting alumina is alumina 5. It has intrinsically a sodium content of 50 ppm.

This starting alumina is impregnated with potassium at different contents.

The impregnation is carried out dry with the aid of a solution of potassium carbonate. The impregnated alumina is then dried overnight at 130° C. and then calcined at 470° C. for 1 h 30 min.

The alumina samples tested are pretreated under a stream of air of nitrogen at 300° C. for 2 hours in order to remove any trace of moisture following their storage and in order to make it possible to compare their effectiveness in identical conditions.

1 g alumina (solids content) thus pretreated is introduced into 200 ml of a solution of cyclohexane containing 1500 ppm (by weight/volume) of p-tert-butylcatechol (TBC). The temperature is maintained at 25° C. After 162 h the content of TBC present in the solution is analysed by UV-visible.

The degree of adsorption of TBC and the mass uptake of the alumina are deduced from this.

The characteristics of the aluminas employed are combined in Table 3.

TABLE 3

| Content of element K (mmol/100 g alumina 5) | % by weight TBC adsorbed | Mass uptake of the alumina (g/100 g) |
|---|---|---|
| 0 | 57 | 17.1 |
| 21 | 57.7 | 17.3 |
| 46 | 63.7 | 19.1 |
| 66 | 73.3 | 22.0 |
| 154 | 60.7 | 18.2 |

What is claimed is:

1. Process for adsorption of polymerization inhibitors from ethylenically unsaturated monomers, in which these inhibitors are placed in contact with an alumina, wherein said alumina is produced by drop coagulation or by extrusion-blending.

2. Process according to claim 1, wherein the alumina has a total pore volume of at least 0.2 ml/g.

3. Process according to claim 1, wherein the alumina has a particle size of between 0.8 and 10 mm.

4. Process according to claim 1, wherein the alumina has a specific surface of at least 10 $m^2/g$.

5. Process according to claim 1, wherein the alumina comprises at least one compound of an element comprising the alkali metals, the rare earths or the alkaline-earth metals.

6. Process according to claim 5, wherein the alumina is doped with at least one compound of one comprising: sodium, potassium, lithium, lanthanum or cerium.

7. Process according to claim 5, wherein the alumina includes at least 5 mmol of at least one element comprising the alkali metals, the rare earths and the alkaline-earth metals per 100 g of alumina.

8. Process according to claim 1, wherein the inhibitor is picric acid, a nitroaromatic, a quinone derivative, a naphthol, an amine, a phosphite, p-methoxyphenol or p-tert-butylcatechol.

9. Process according to claim 1, wherein the alumina is placed in contact with a mixture of ethylenically unsaturated monomer and of inhibitor.

10. Process according to claim 9, wherein the mixture of ethylenically unsaturated monomer and of inhibitor includes 2 to 2000 ppm by weight per volume of inhibitor.

11. The process according to claim 2, wherein the alumina has a total pore volume of at least 0.3 ml/g.

12. The process according to claim 3, wherein the alumina has a particle size of between 1 and 5 mm.

13. The process according to claim 4, wherein the alumina has a specific surface of at least 50 $m^2/g$.

14. The process according to claim 7, wherein the alumina includes not more than 400 mmol of at least one element comprising the alkali metals, the rare earths and the alkaline earth metals per 100 g of alumina.

15. The process according to claim 14, wherein the alumina includes between 10 and 400 mmol of at least one element comprising the alkali metals, the rare earths and the alkaline earth metals per 100 g of alumina.

16. The process according to claim 8, wherein the quinone derivative is hydroquinone or benzoquinone.

17. The process according to claim 10, wherein the mixture of ethylenically unsaturated monomer and of inhibitor includes 5 to 1500 ppm by weight per volume of inhibitor.

* * * * *